United States Patent [19]
Bowen

[11] Patent Number: 5,827,246
[45] Date of Patent: Oct. 27, 1998

[54] VACUUM PAD FOR COLLECTING POTENTIALLY HAZARDOUS FLUIDS

[75] Inventor: Michael L. Bowen, Arlington, Tex.

[73] Assignee: Tecnol Medical Products, Inc., Fort Worth, Tex.

[21] Appl. No.: 608,118

[22] Filed: Feb. 28, 1996

[51] Int. Cl.⁶ ............................................. A61M 1/00
[52] U.S. Cl. ................................... 604/313; 604/317
[58] Field of Search .................................. 604/313–317, 604/902; 128/846–852, 400, 402, 403; 396/441; 355/77, 73, 75, 76

[56] References Cited

U.S. PATENT DOCUMENTS

| | | | |
|---|---|---|---|
| 3,157,101 | 11/1964 | Rabinow | 396/441 |
| 3,413,903 | 12/1968 | Maldareeli | 396/441 |
| 3,520,300 | 7/1970 | Flower, Jr. | 128/276 |
| 3,572,228 | 3/1971 | Ternes | 396/441 |
| 3,783,863 | 1/1974 | Kliever | 128/134 |
| 3,813,682 | 5/1974 | Nishikawa et al. | 396/441 |
| 3,929,135 | 12/1975 | Thompson | 128/287 |
| 4,248,651 | 2/1981 | Kojimoto et al. | 156/198 |
| 4,525,166 | 6/1985 | Leclerc | 604/133 |
| 4,533,352 | 8/1985 | Van Beek et al. | 604/317 |
| 4,679,580 | 7/1987 | Devall et al. | 137/39 |
| 4,679,590 | 7/1987 | Hergenroeder | 137/602 |
| 4,729,404 | 3/1988 | Hergenroeder | 137/602 |
| 4,760,928 | 8/1988 | Bustos | 211/59.4 |
| 4,803,813 | 2/1989 | Fiterman | 52/199 |
| 4,828,894 | 5/1989 | Taylor | 428/53 |
| 5,014,389 | 5/1991 | Ogilvie et al. | 15/353 |
| 5,034,006 | 7/1991 | Hosoda et al. | 604/317 |
| 5,176,667 | 1/1993 | DeBring | 604/356 |
| 5,192,276 | 3/1993 | Gatti | 604/313 |
| 5,215,539 | 6/1993 | Schoolman | 604/280 |
| 5,304,056 | 4/1994 | Fetterhoff | 425/304 |
| 5,346,264 | 9/1994 | Law et al. | 285/158 |
| 5,380,278 | 1/1995 | Mombrinie | 604/35 |
| 5,437,651 | 8/1995 | Todd et al. | 604/313 |
| 5,484,427 | 1/1996 | Gibbons | 604/313 |
| 5,486,932 | 1/1996 | Leonard | 355/73 |
| 5,549,584 | 8/1996 | Gross | 604/313 |
| 5,563,683 | 10/1996 | Kamiya | 355/73 |

*Primary Examiner*—John G. Weiss
*Assistant Examiner*—David J. Cho
*Attorney, Agent, or Firm*—Dority & Manning, P.A.

[57] ABSTRACT

A system for collecting fluids from medical procedures, laboratory testing or industrial processes using a vacuum pad placed on the floor or an appropriate supporting structure adjacent to a potential source of hazardous fluids. The vacuum pad is formed from corrugated panels having a first sheet and a second sheet with a plurality of corrugated ribs to provide fluid flow channels between the first sheet and the second sheet. A manifold is provided as a part of the vacuum pad to supply a relatively uniform amount of vacuum to each fluid flow channel. The vacuum pad and a container for potentially hazardous fluids may be coupled in series by one or more conduits to a vacuum source such as commonly available in surgical operating rooms.

28 Claims, 5 Drawing Sheets

VACUUM PAD FOR COLLECTING POTENTIALLY HAZARDOUS FLUIDS

TECHNICAL FIELD OF THE INVENTION

This invention relates in general to the field of collecting potentially hazardous fluids associated with medical procedures, laboratory testing, and various industrial procedures which may produce potentially hazardous fluids. In particular, this invention relates to forming a vacuum pad from corrugated panels for use as part of a hazardous fluid collection system.

BACKGROUND OF THE INVENTION

Many industrial processes produce potentially hazardous fluids which must be collected, stored and disposed of in accordance with applicable health, safety and environmental rules and regulations. Health and safety of personnel working in the vicinity of potentially hazardous fluids and preventing environmental damage are major concerns for all industries. Therefore, cleanliness standards and personnel protection requirements which at one time may have only been associated with surgical operating rooms and special clean rooms are now frequently a part of many routine business procedures.

Many medical procedures such as orthoscopic surgery or treating severe burns may use large volumes of fluid to irrigate or bathe the region of the medical procedure. During orthoscopic surgery on a knee joint, several gallons of saline solution may be forced under pressure into the knee joint. During treatment of burn patients, relatively large volumes of water with various antiseptic compounds may be used to clean and disinfect the burn area. Waste fluids from such medical procedures present a safety hazard to personnel if the fluids are permitted to drain in an uncontrolled manner onto the floor of the medical facility. Such waste fluids may contain bacteria and other microorganisms which present serious contamination hazards to both personnel working at the medical facility, visitors and other patients.

Increased concern for infection of healthcare personnel from airborne pathogens such as tuberculosis and hepatitis B virus have resulted in increased emphasis on personnel protection and eliminating potential sources of contamination. Any uncontrolled fluid within a medical facility is a potential source of highly dangerous bacteria and contaminated aerosols. Many of the viral hemorrhagic fevers such as Yellow fever, Red Valley fever, and perhaps Rocky Mountain spotted fever, rabies and small pox can be transmitted through aerosols. Such aerosols may be generated not only by exhalation of an infected patient but also by various medical procedures and processes that impart energy to a microbial suspension including uncontrolled fluids on an operating room table or floor.

Apparatus including a suction head for aspirating fluid from an operating room floor is shown in U.S. Pat. No. 5,014,538 entitled "Foot Manipulated Suction Head And Method For Employing Same". A mat for use in collecting fluid on an operating room is shown in U.S. Pat. No. 4,729,404, entitled "Receptacle For Collecting Fluid". A suction manifold for collecting fluid in proximity to a wound or incision is shown in U.S. Pat. No. 5,215,532, entitled "Vacuum Strip Apparatus For Surgery". An annular suction ring for continuously evacuating fluid from a surgical area is shown in U.S. Pat. No. 5,380,278, entitled "Liquid Cleansing And Evacuation Method And Apparatus For Use In Surgical Procedures". Each of the preceding patents is incorporated by reference for all purposes within this application.

Corrugated plastic panels and boards have been satisfactorily used for a wide variety of products as represented by U.S. Pat. No. 4,760,928, entitled "Corrugated Sheet Plastic Beverage Display Case"; U.S. Pat. No. 4,803,813 entitled, "Foldable Corrugated Plastic Roof Ventilator", and U.S. Pat. No. 4,828,894, entitled "Corrugated Plastic Board Assemblies". Also, various processes are well known to form a wide variety of articles from corrugated plastic material. U.S. Pat. No. 4,428,651, entitled "Thermal Forming Process of Corrugated Plastic Board" discloses one example of these processes. U.S. Pat. No. 5,304,056, entitled "Apparatus for Sealing Edges of Corrugated Plastic Material" provides further examples of fabricating techniques using corrugated plastic material. Each of the preceding patents is incorporated by reference for all purposes within this application.

SUMMARY OF THE INVENTION

In accordance with teachings of the present invention, disadvantages and problems associated with previous equipment and methods for collecting potentially hazardous fluids have been substantially reduced or eliminated. The present invention includes a vacuum pad fabricated from corrugated material with a plurality of openings in one side of the pad to allow potentially hazardous fluids to flow into the corrugated material. The opposite side of the pad provides a fluid impervious barrier to prevent the potentially hazardous fluids from contacting the floor or supporting structure on which the pad is resting. A manifold is formed as part of the pad for connection to a source of vacuum such that potentially hazardous fluids may be drawn through the holes in the pad, the corrugated material, the manifold and into an appropriate container. The vacuum pad may be used for many functions such as collecting fluids which fall from an operating room table.

Technical advantages of the present invention include fabricating the vacuum pad from relatively low cost corrugated material such as corrugated plastic panels. As a result, the vacuum pad may be disposed of after a single medical procedure. Alternatively, the vacuum pad may be satisfactorily used at a laboratory work station for a selected period of time such as a week, a month, or longer depending upon the amount of activity at the specific work station, the type of potentially hazardous fluid and the material used to fabricate the vacuum pad. The vacuum pad may be used with a source of relatively low level suction which is typically available in a surgical operating room. In accordance with one aspect of the present invention, skid-resistant material may be placed on the side of the vacuum pad resting on the floor or other supporting structure.

One aspect of the present invention includes providing forming a vacuum pad from a corrugated plastic panel having a first sheet and a second sheet with a plurality of corrugated ribs disposed between the first sheet and the second sheet. Fluid flow channels are formed between the first sheet and the second sheet by the respective corrugated ribs. A number of small holes may be formed in the first sheet of the corrugated plastic panel to allow fluid communication between the exterior of the vacuum pad and respective fluid flow channels. A manifold is preferably attached to the fluid flow channels for use in applying a relatively uniform vacuum to each fluid flow channel to draw fluids through the openings in the first sheet, through the fluid flow channels and into the manifold. A flexible hose or conduit may be used to connect the manifold to a source of vacuum. A container may also be included between the manifold and the source of the vacuum to collect liquids and/or small particulate matter drawn through the openings in the first sheet.

Further technical advantages resulting from fabricating a vacuum pad from corrugated plastic panels in accordance with the teachings of the present invention include providing a relatively thin pad which may be easily adapted to various geometric configurations. In addition to relatively low cost, corrugated plastic panels are relatively strong and are not easily crushed by walking or standing on the vacuum pad or by placing heavy equipment on the vacuum pad. If the corrugated material is crushed or deformed it has high resiliency and tends to return to its original configuration. When large quantities of liquid are placed on the exterior of the vacuum pad, the difference in pressure between the fluid flow channels and the exterior of the vacuum pad increases resulting in higher flow through the openings and the fluid flow channels into the manifold. The perimeter of corrugated plastic panels can be easily heat sealed to provide both a smooth transition with the associated supporting structure and to prevent undesired fluid flow along the perimeter of the panels.

A corrugated panel incorporating teachings of the present invention can be attached to a source of low level vacuum such as a home vacuum cleaner and used in a small photographic laboratory to hold photographic film and photographic paper during the process of developing and printing pictures. This embodiment of the present invention is particularly beneficial for hobby photographers with a home film developing laboratory.

BRIEF DESCRIPTION OF THE DRAWINGS

For a more complete understanding of the present invention and the advantages thereof, reference is now made to the following written description taken in conjunction with the accompanying drawings, in which.

DETAILED DESCRIPTION OF THE INVENTION

The preferred embodiments of the present invention and its advantages are best understood by referring to FIGS. 1–16 of the drawings, like numerals being used for like and corresponding parts of the various drawings.

Figure 1:
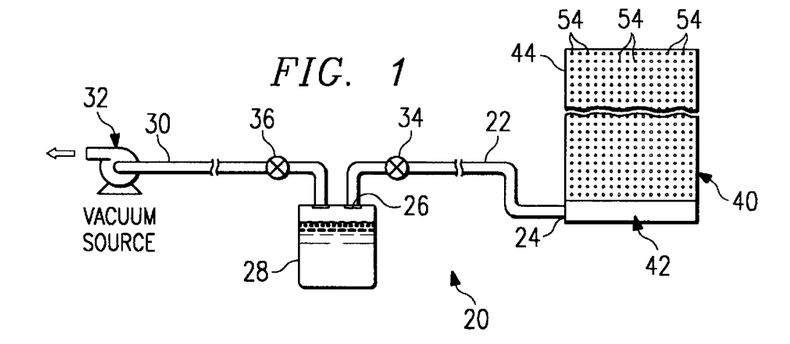
FIG. 1 is a schematic drawing showing a system having a vacuum pad for use in collecting potentially hazardous fluids.

Fluid collection system 20 with vacuum pad 40 incorporating teachings of the present invention is shown in FIG. 1. Vacuum pad 40 includes manifold or fluid collection chamber 42. One end 24 of first conduit 22 is attached to and provides fluid communication with manifold 42. The other end 26 of first conduit 22 is attached to container 28. Second conduit 30 extends between container 28 and vacuum source 32. Appropriately sized valves 34 and 36 may be provided in respective conduits 22 and 30 to control fluid flow therethrough. As will be discussed later in more detail, coupling vacuum pad 40 with vacuum source 32 allows fluid collection system 20 to safely collect a wide variety of potentially hazardous fluids.

For purposes of this patent application, the term "fluid" includes any gas, liquid, or mixture of gas and liquid. Various types of particulate matter and/or aerosols may be entrained with such fluids. The term "aerosols" is defined as any insoluble liquid or particulate matter in a gaseous suspension. Aerosols are frequently associated with microbial solutions. Droplett nuclei may also be considered an aerosol.

For some applications first conduit 22 and/or second conduit 30 may be flexible hoses to accommodate varying the location of vacuum pad 40 and container 28 relative to vacuum source 32. For other applications, first conduit 22 and/or second conduit 30 may be part of a fixed network of tubing and hoses (not expressly shown) to collect potentially hazardous fluids at a medical facility, laboratory, or industrial plant.

Vacuum source 32 may be a wall suction port (not expressly shown) such as commonly found in surgical operating rooms for supplying relatively low level suction of approximately three hundred millimeters (300 mm) of mercury below atmospheric pressure. Alternatively, vacuum source 32 may be a portable blower that can be easily moved to various locations within a facility. A wide variety of fittings and connections may be used to attach first conduit 22 with manifold 42 and container 28. Similarly, a wide variety of fittings and connections may also be used to attach second conduit 30 with container 28 and vacuum source 32.

Suction or vacuum from vacuum source 32 is applied through second conduit 30 to container 28 and then through first conduit 22 to vacuum pad 40. Vacuum source 32 will normally draw air from the exterior of vacuum pad 40 through first conduit 22. Liquids falling onto the exterior of vacuum pad 40 will also be drawn through first conduit 22. Depending upon the specific application, aerosols and small particulate matter may also be drawn through conduit 22.

Upon reaching container 28, liquids and any entrained particulate matter will generally be sufficiently heavy in relation to the relatively low amount of suction and resulting air velocity to drop into container 28 for collection and eventual disposal. For some applications, filters and/or baffles (not shown) may be installed within container 28 to assist with removing liquids, aerosols and small particulate matter entrained with air flowing through first conduit 22. Preferably, air flowing from container 28 through second conduit 30 will be relatively free of any liquids, aerosols or particulate matter.

Depending upon the type of potentially hazardous fluid and the specific configuration of container 28, one or more vent control valves may be installed as part of container 28 to prevent undesired liquid overflow. U.S. Pat. No. 4,679,580, entitled "Vapor Vent Control Valve" is representative of one type of valve that may be satisfactorily used with container 28. Also, valve 36 may include features similar to those shown in U.S. Pat. No. 4,679,580 to automatically prevent liquid from flowing through second conduit 30 to vacuum source 32.

For some applications, such as large laboratories or pharmaceutical manufacturing facilities, a number of vacuum pads 40 may be used to collect potentially hazardous fluids from various locations within the facility. For such applications, vacuum source 32 may be a complex system of filters, containers, ion exchangers and other components associated with safe handling and disposal of potentially hazardous fluids. Fluid collection system 20 as shown in FIG. 1 represents only one example for using a vacuum pad incorporating teachings of the present invention.

Vacuum pad 40 is preferably fabricated from relatively low cost material to allow disposal after a single surgical or medical procedure. First conduit 22 may also be formed from disposable material such as plastic hose. For one application clear, acrylic hose approximately one half inch in diameter was satisfactorily used. The use of a clear plastic hose allows visual monitoring of the performance of vacuum pad 40. When a number of vacuum pads 40 are installed at a large laboratory or pharmaceutical manufacturing facility, a routine maintenance procedure can be established to dispose of each vacuum pad 40 on a periodic basis as appropriate for the potentially hazardous fluid or fluids produced at each facility.

Vacuum pad 40, as shown in FIGS. 1–4 may be formed from a corrugated plastic panel which may also be referred to as a corrugated plastic board. Other types of corrugated material having desired characteristics of easy manufacture and assembly along with fluid flow channels to contain potentially hazardous fluids may be satisfactorily used to form vacuum pad 40. Wax coated cardboard is an example of another type of corrugated material satisfactory for use with the present invention.

Corrugated plastic panels formed from polypropylene are often available at relatively low cost when purchased in large quantities. Various thermoplastic polymers in addition to polypropylene may be used to form corrugated plastic panels satisfactory for use with the present invention. One of the benefits of the present invention includes the ability to select a thermoplastic polymer and one or more additives as appropriate for the specific potentially hazardous fluids that will be collected using the resulting vacuum pad.

Corrugated plastic panels satisfactory for use with the present invention may be obtained from various sources. One source is Coroplast, Inc. located at 4501 Spring Valley Rd., Dallas, Tex. Corrugated plastic panels are available in a wide variety of colors and can be easily formed into various geometric configurations as required for each application.

Vacuum pad 40 as shown in FIGS. 1–4 is formed from corrugated plastic panel 44 having first sheet 46 and second sheet 48 with a plurality of corrugated ribs 50 disposed therebetween. First sheet 46, second sheet 48 and corrugated ribs 50 are formed as integral parts of corrugated plastic panel 44. A plurality of fluid flow channels 52 are formed between first sheet 46 and second sheet 48 by respective corrugated ribs 50. A plurality of openings 54 are formed in first sheet 46 to allow fluid communication between the exterior of vacuum pad 40 and respective fluid flow channels 52.

The number, the size and the location of each opening 54 in first sheet 46 may be varied depending upon the intended application for the resulting vacuum pad 40. For example, FIGS. 1–4 show each opening 54 having a generally circular configuration and uniformly spaced with respect to each other. For some applications, openings 54 may be slots or slits as compared to circular openings. Also, the number of openings 54 may be concentrated in one or more portions of first sheet 46. Preferably, more than one opening 54 will be formed in first sheet 46 for each fluid flow channel 52. Providing multiple opening 54 in each flow channel 52 tends to improve the fluid flow therethrough.

Varying the density of openings 54 may be particularly beneficial if vacuum pad 40 is relatively large and will be used to collect potentially hazardous fluids from multiple sources. For such applications, the number of openings 54 through first sheet 46 may be increased immediately adjacent to a potential hazardous fluid source while the number of openings 54 may be decreased in locations which are not directly adjacent to a potential source of hazardous fluid. Openings 54 may be formed from various types of sharp piercing tools and/or drills depending upon the specific type of material used to form corrugated plastic panel 44. During the fabrication of vacuum pad 40 from relatively thin (one to twenty millimeters thick) corrugated plastic panels 44 care must be taken to ensure that the residue from forming openings 54 does not block or obstruct fluid flow in the respective fluid flow channels 52.

Figure 2:
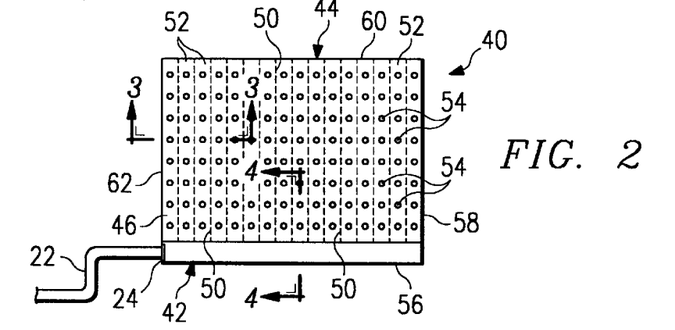
FIG. 2 is a schematic drawing showing a plan view of a vacuum pad satisfactory for use in collecting potentially hazardous fluids.

As shown in FIGS. 1–4, vacuum pad 40 has a generally rectangular configuration defined in part by first edge 56, second edge 58, third edge 60 and fourth edge 62. As best shown in FIG. 2, each fluid flow channel 52 preferably extends longitudinally from third edge 60 to first edge 56. Manifold 42 is attached to and forms a part of first edge 56. For many applications vacuum panel 44 will preferably have a thickness in the range of one millimeters to twenty millimeters.

Figure 3A:
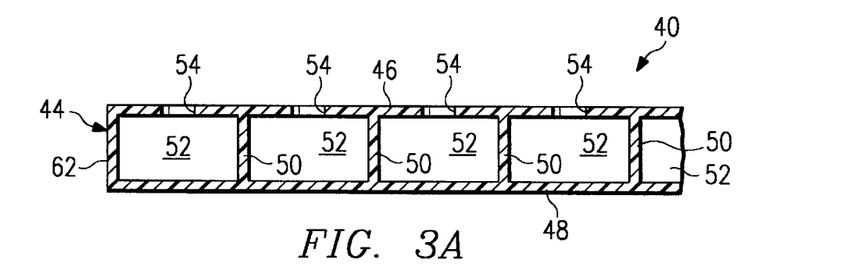
FIG. 3A is a drawing in section with portions broken away of the vacuum pad taken along lines 3—3 of FIG. 2.
Figure 4:
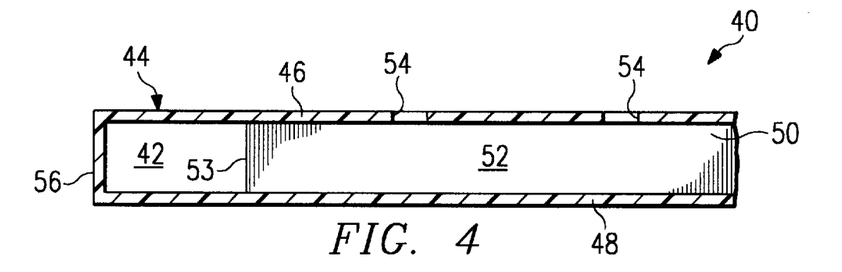
FIG. 4 is a drawing in section with portions broken away showing portions of the manifold attached to the vacuum pad taken along lines 4—4 of FIG. 2.

As best shown in FIG. 3A, fluid flow channels 52 are disposed adjacent to each other extending laterally from fourth edge 62 to second edge 58. Corrugated ribs 50 direct potentially hazardous fluid flow from openings 54 longitudinally through the associated fluid flow channel 52 to manifold 42. Corrugated ribs 50 prevent fluid flow laterally between adjacent fluid flow channels 52. As shown in FIGS. 3A and 4, second sheet 48 preferably provides a fluid impervious barrier to prevent potentially hazardous fluids within each longitudinal flow channel 52 from contacting the floor or other supporting structure on which the associated vacuum pad 40 is resting.

By forming vacuum pad 40 from relatively thin corrugated plastic panel 44, corrugated ribs 50 will tend to return the associated fluid flow channels 52 to their original configuration after being crushed or deformed. Therefore, walking and standing on vacuum pad 40 will generally not adversely affect its ability to collect potentially hazardous fluids. Also, chairs and other types of equipment may be placed upon or rolled across vacuum pad 40 without permanently deforming fluid flow channels 52.

Figure 3B:
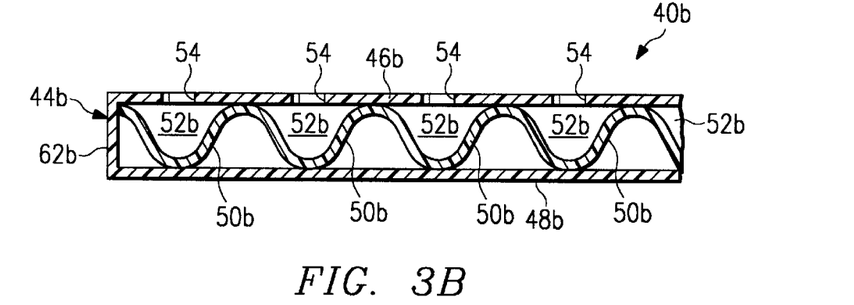
FIG. 3B is a drawing in section with portions broken away showing an alternative configuration for a vacuum pad incorporating teachings of the present invention.

Vacuum pad 40*b*, as shown in FIG. 3B, is substantially the same as vacuum pad 40 shown in FIG. 3A. Vacuum pad 40*b* includes a plurality of fluid flow channels 52*b* formed by corrugated ribs 50*b* having a generally sanusoidal or wavy configuration between first sheet 46*b* and second sheet 48*b*. Depending upon the intended application, fluid flow channels may be formed in a vacuum pad having cross-sections other than generally rectangular as shown in FIG. 3A for vacuum pad 40 or sanusoidal as shown for vacuum pad 40*b* in FIG. 3B.

As will be discussed later in more detail, the teachings of the present invention provide various techniques to form or attach a manifold with a plurality of fluid flow channels provided by a corrugated panel. For vacuum pad 40 as shown in FIG. 4, the length of each corrugated rib 50 is less than the distance between first edge 56 and third edge 60 such that each corrugated rib 50 terminates at end 53 to form manifold or fluid collection chamber 42 between ends 53 and first edge 56 of corrugated plastic panel 44.

For some applications, vacuum pad 40 is preferably formed with one or more layers of hydrophillic material to prevent liquid puddles from forming on the exterior surface of first sheet 46 between openings 54 and assists with providing a more uniform suction to pull any liquids falling on first sheet 46 through the associated openings 54. Various types of woven and non-woven material may be satisfactorily attached to the exterior of first sheet 46 using adhesives, sonic bonding and/or heat sealing as appropriate for the type of thermoplastic material used to form corrugated plastic panel 44 and the specific type of absorbent material. In addition to improving the fluid collecting characteristics of vacuum pad 40, placing one or more absorbent material layers on the exterior surface of first sheet 46 will substantially reduce noise created by suctioning liquid through openings 54. For some applications, vacuum pad 40 will be too noisy without placing a covering on the exterior surface of first sheet 46.

Figure 5:
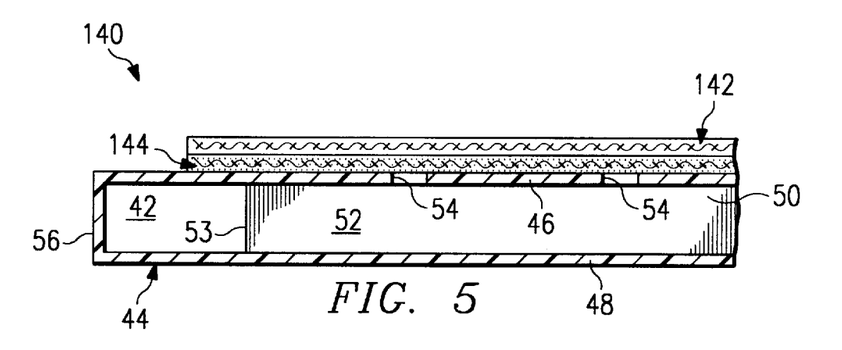
FIG. 5 is a drawing in section with portions broken away showing a layer of hydrophillic material and a perforated layer attached to an exterior surface of the vacuum pad of FIG. 4.

Vacuum pad 140 incorporating an alternative embodiment of the present invention is shown in FIG. 5. Vacuum pad 140 is similar in many respects to vacuum pad 40, including the use of corrugated plastic panel 44. For the embodiment of the present invention as shown in FIG. 5, two layers of material 142 and 144 have been placed on the exterior of first sheet 46 covering holes 54. First material layer 142 provides a perforated layer which allows fluid flow from the exterior of vacuum pad 40 through first layer 142 and second layer 144 through holes 54 and into the corresponding fluid flow channels 52.

Further description and operation of barrier material satisfactory for use as first material layer 142 may be found in U.S. Pat. No. 3,929,135.

First layer 142 preferably forms a fluid resistant barrier with respect to any liquids which might tend to flow outwardly from fluid flow channel 52 through openings 54 and second layer 144. First layer 142 may be described as a liquid barrier which allows fluid flow in one direction towards fluid flow channels 52 and resists the flow of liquids in the opposite direction away from fluid flow channels 52.

Second material layer 144 is preferably formed from wicking material to assist in drawing any liquids falling on the exterior of vacuum pad 140 through first layer 142. Second layer 144 also cooperates with the associated openings 54 to provide a more uniform suction with respect to such liquids. First layer 142 and/or second layer 144 will tend to accumulate small particulate matter (not shown) falling on the exterior of vacuum pad 140 depending upon dimensions of the particulate matter and dimensions of interstices (not shown) or perforations (not shown) in layers 142 and 144. With respect to vacuum pad 40, any small particulate matter having a diameter less than the diameter of openings 54 will tend to migrate through openings 54 and into the corresponding fluid flow channels 52.

First material layer 142 is preferably formed from perforated or porous plastic material with allows fluid flow from the exterior of vacuum pad 140 through first material layer 142 and second material layer 144 into the associated holes 54. Second material layer 144 is preferably formed from an absorbent, heat sealable, non-woven fabric. First material layer 142 and second material layer 144 are preferably selected to cooperate with each other such that second material layer 144 is selected to have good wicking action with respect to first material layer 142. For one application, VISPORE plastic film, available from Tredegar Film Products, has been satisfactorily used as first material layer 142. HYDROKNIT® absorbent material, available from Kimberly-Clark, has been satisfactorily used as second material layer 144 in combination with Vispore material in first material layer 142.

First layer 142 and second layer 144 may be bonded or laminated to each other. In areas where first layer 142 does not directly contact second layer 144, puddles of liquid may form on the exterior surface of first layer 142. Material layers 142 and 144 may be laminated with each other using ultrasonic or other bonding techniques. Alternatively, first layer 142 may be stretched tightly over second layer 144 and layers 142 and 144 may be bonded together only around the perimeter of suction pad 40.

Figure 6:
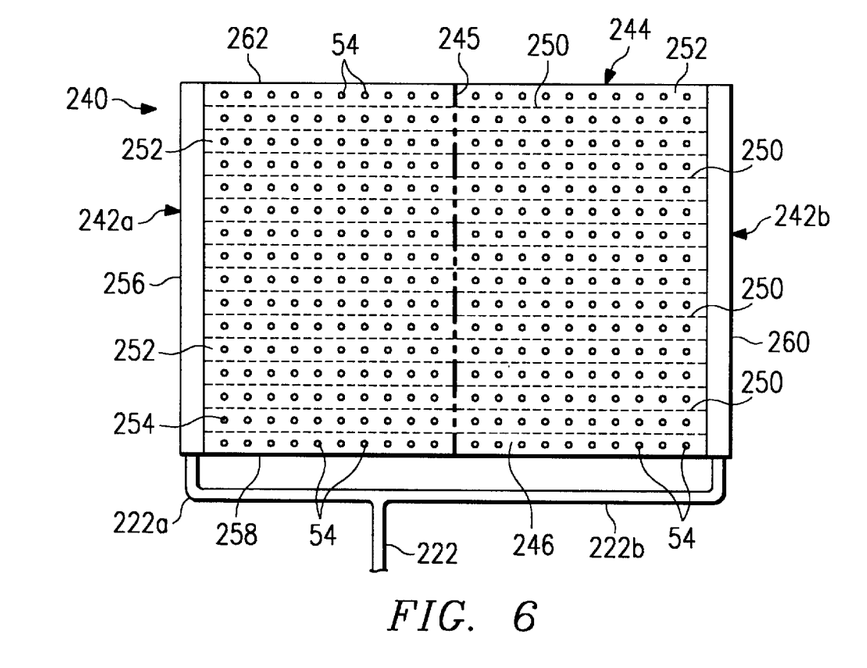
FIG. 6 is a schematic drawing showing a plan view of a vacuum pad having a pair of manifolds attached along opposite edges of the vacuum pad and a fold line extending through approximately the middle of the vacuum pad.

Vacuum pad 240, incorporating an alternative embodiment of the present invention, is shown in FIG. 6. Vacuum pad 240 may be formed from corrugated panel 244 similar to corrugated plastic panel 44 used to fabricate vacuum pads 40 and 140. Corrugated panel 244 has a generally rectangular configuration defined in part by first edge 256, second edge 258, third edge 260 and fourth edge 262. For this particular embodiment of the present invention, corrugated panel 244 includes fold or flexible seam 245 which extends laterally from second edge 258 to fourth edge 262. A pair of manifolds or fluid collection chambers 242*a* and 242*b* are attached to opposite ends of fluid flow channels 252 along respective edges 256 and 260. Corrugated ribs 250 are shown as dotted lines in FIG. 6.

As shown in U.S. Pat. No. 4,803,813 and 4,828,894, corrugated plastic panels or corrugated plastic boards may be easily folded into various configurations. Flexible seam 245 is preferably formed generally parallel with and equal distance between manifolds 242*a* and 242*b*. By placing flexible seam 245 laterally across corrugated panel 244, it is possible to fold vacuum pad 240 in half for shipment and storage prior to use. Also, the ability to fold vacuum pad 240 in half facilitates cleanup and disposal after vacuum pad 240 has been used to collect potentially hazardous fluids. This feature is particularly important if one or more layers of absorbent material have been placed on exterior surface 246 of vacuum pad 240.

Conduit 222 may be used to attach vacuum pad 240 to an appropriate source of vacuum as previously described with respect to vacuum pad 40. As best shown in FIG. 6 the end of conduit 222 adjacent to vacuum pad 240 preferably includes first portion 222a which is attached to first manifold 242a and second portion 222b which is attached to second manifold 242b. First portion 222a and second portion 222b provide fluid communication with respective first manifold 242a and 242b and conduit 222 to allow a source of vacuum to draw liquids from the exterior of vacuum pad 240 through holes 54 in exterior surface 246 into fluid flow channels 252 and first manifold 242a and second manifold 242b.

Figure 7:
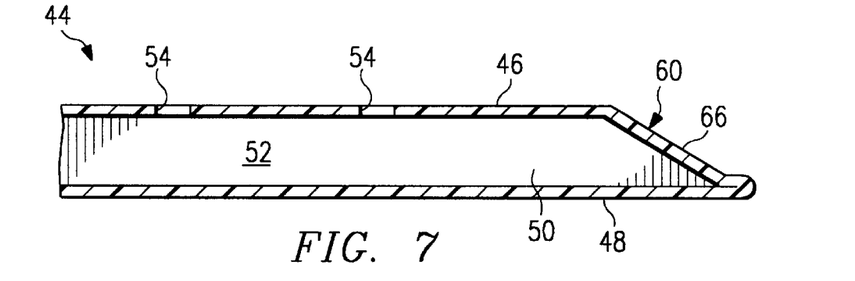
FIG. 7 is a drawing in section with portions broken away showing one edge of a vacuum pad which has been heat sealed to provide both a fluid barrier and a smooth transition with adjacent portions of the floor.

FIG. 7 shows one configuration for third edge 60 of corrugated plastic panel 44 which may be used to form either vacuum pad 40 or vacuum pad 140. One of the benefits of using corrugated plastic panels to form vacuum pads 40 and 140 includes the ability to seal the ends fluid flow channels 52 opposite from fluid collection chamber 42. This feature of corrugated plastic panels or corrugated plastic board is described in more detail in U.S. Pat. No. 5,304,056.

As shown in FIG. 7, third edge 60 preferably includes tapered portion 66 extending between first sheet 46 and second sheet 48. The dimensions of tapered portion 66 are preferably selected to provide a relatively smooth transition from the floor (not shown) or other supporting structure on which either vacuum pad 40 or vacuum paid 140 is resting. For some applications it may be desirable to form a similar tapered portion along the other edges 56, 58 and 62.

For many applications a fluid tight seal is preferably formed along third edge 60. However, vacuum pad 40 and 140 may function satisfactorily even though one or more small holes or defects may be present along third edge 60. Depending upon the capacity of the vacuum source attached to manifold or fluid collection chamber 42, vacuum pads 40 and 140 may function satisfactorily even though a defect such as a split or opening may occur along edges 56, 58, 60 and/or 62 as long as sufficient vacuum can be maintained within fluid flow channels 52 to draw potentially hazardous fluids into manifold 42. One of the benefits of the present invention is that vacuum pads 40 and 140 may continue to function satisfactorily despite minor damage and/or abuse to corrugated panel 44.

Figure 8:
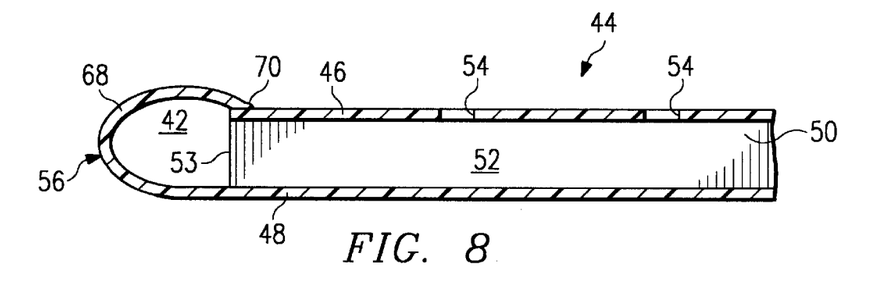
FIG. 8 is a drawing in section with portions broken away showing an alternative configuration to form a manifold extending longitudinally along one edge of a vacuum pad in accordance with teachings of the present invention.

FIG. 8 shows edge 56 of corrugated panel 44 with an alternative configuration to form manifold or fluid collection chamber 42. Portions of top sheet 46 and ribs 50 adjacent to edge 56 have been cut away leaving tab or flap 68 of second sheet 48 extending from ends 53 of ribs 50. Flap 68 of second sheet 48 may then be folded and welded to the exterior surface of first sheet 46 to form manifold or fluid collection chamber 42 extending laterally along edge 56. Extreme outer portion 70 of flap 68 may be bonded with the exterior surface of first sheet 46 using various techniques such as adhesives, heat sealing or sonic bonding as appropriate for the specific type of material used to form corrugated panel 44. Corrugated plastic panels are well suited for this fabrication technique. For some applications multiple folds or cuts (not expressly shown) may be formed laterally across fluid flow channels 252 to allow corrugated plastic panel 244 to be rolled up when not in use.

Figure 9:
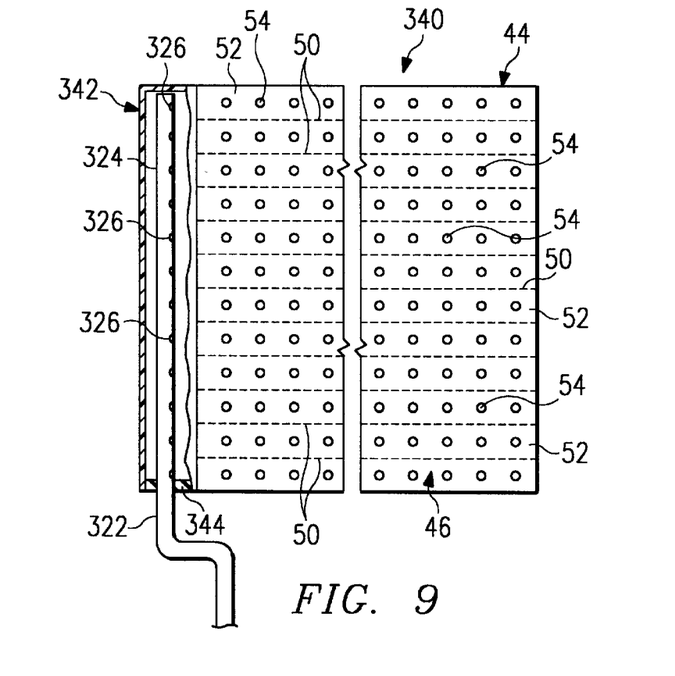
FIG. 9 is a drawing in section with portions broken away showing a perforated conduit disposed within a manifold extending along one edge of a vacuum pad in accordance with teachings of the present invention.

Vacuum pad 340 incorporating a further embodiment of the present invention is shown in FIG. 9. Vacuum pad 340 may be formed from corrugated plastic panel 44 as previously described with respect to vacuum pads 40 and 140. Manifold 342 and conduit 322 represent the principal differences between vacuum pad 340 and vacuum pad 40. Conduit 322 preferably includes a perforated portion 324 having a plurality of openings 326 formed therein. Manifold 342 includes end 344 with an appropriately sized opening to allow inserting perforated portion 324 of conduit 322 therein. End 344 of manifold 342 also forms a fluid seal with the exterior of first conduit 322. Openings 326 are preferably loosely aligned with corresponding fluid flow channels 52.

When vacuum or suction is applied from an appropriate source to conduit 322, fluids, including air and any liquids falling on the exterior of first sheet 46, will be drawn through holes 54, the respective fluid flow channels 52 into manifold or fluid collection chamber 342 and then into conduit 322 through holes 326. Depending upon the thickness of corrugated panel 44, it may be possible to form perforated portion 324 from relative stiff material and insert perforated portion 324 laterally through corrugated ribs 50. Appropriately sized holes (not shown) may be drilled laterally through corrugated ribs 50 or corrugated ribs 50 may be pierced laterally.

Figure 10:
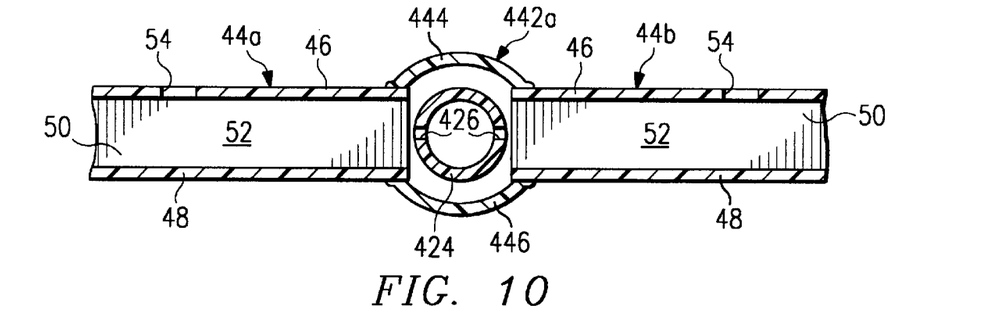
FIGS. 10–15 are drawings in section with portions broken away showing alternative configurations for attaching or coupling a manifold with fluid flow channels of a vacuum pad in accordance with teachings of the present invention.

FIGS. 10–13 show various alternative configurations to form manifold or fluid collection chambers 442a–d with a pair of corrugated panels 44a and 44b extending laterally therefrom. The ends of corrugated panels 44a and 44b (not shown in FIGS. 10–14) opposite from manifolds 442a–d are preferably sealed to prevent undesired fluid flow therefrom. As shown in FIG. 10, portion 424 of a fluid conduit is preferably disposed within manifold 442a with a plurality of holes 426 formed therein and loosely aligned with respective fluid flow channels 52. Holes 426 in cooperation with conduit 424 and longitudinal flow channels 52 allow communicating a source of vacuum with each longitudinal flow channel 52 to draw fluids from the exterior of corrugated panels 44a and 44b through holes 54. As show if FIG. 10, manifold 442a has been formed by bonding or welding material strip 444 to the exterior of first sheets 46 of adjacent corrugated panels 44a and 44b. In a similar manner material strip 446 has been welded or bonded to the exterior surface of adjacent second sheets 48 of adjacent corrugated panels 44a and 44b.

Figure 11:
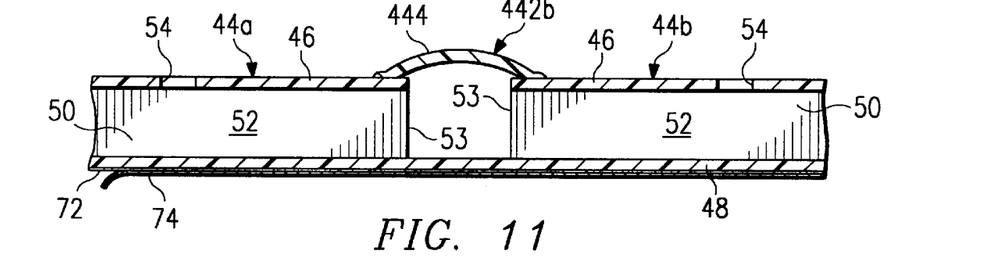

Fluid collection chamber 442b as shown in FIG. 11 may be formed by initially cutting a slot or trough laterally through first sheet 46 and corrugated ribs 50. As a result corrugated panel 44 is divided into two portions 44a and 44b with ends 53 of corrugated ribs 50 facing each other. For this particular embodiment, second sheet 48 has not been cut and provides a mechanical coupling between portions 44a and 44b. Thus, it is only necessary to attach material strip 444 to the exterior of top sheets 46 on adjacent portions 44a and 44b.

For some applications, it may be desirable adhesive layer 72 on the exterior of second sheet 48 along with removable protective covering 74. Adhesive layer 72 may extend across substantially all of the exterior surface of second sheet 48 or adhesive layer 72 may be disposed in a pattern on the exterior surface of second sheet 48. Various types of material such as a thin layer of paper may be satisfactorily used as removable protective covering 74. Also, various types of anti-skid material (not expressly shown) may be placed on the exterior of second sheet 48 depending upon the specific application for the resulting vacuum pad.

Figure 12:
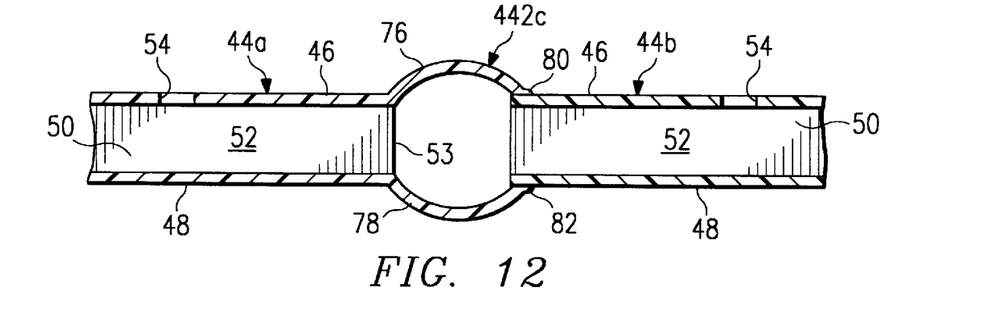

As shown in FIG. 12, corrugated panel 44a includes flap 76 extending from first sheet 46 and flap 78 extending from second sheet 48. Extreme outer portion 80 of flap 76 is bonded to first sheet 46 of corrugated panel 44b. Extreme outer portion 82 of flap 78 is bonded to the adjacent portion of second sheet 48 of corrugated panel 44b. Flaps 76 and 78 cooperate with each other to form fluid collection chamber or manifold 442c between corrugated panels 44a and 44b.

Figure 13:
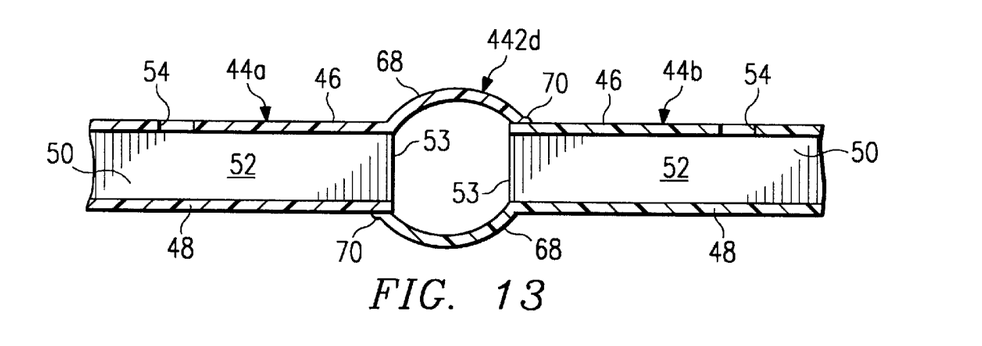

Corrugated panels 44a and 44b as shown in FIG. 13 include respective flaps 68 extending from ends 53 of corrugated ribs 52. Fluid collection chamber 442d is formed between corrugated panels 44a and 44b by attaching extreme end 70 of flap 68 with the exterior of first surface 46 and extreme outer portion 70 of flap 68 with the adjacent exterior of second sheet 48.

Figure 14:
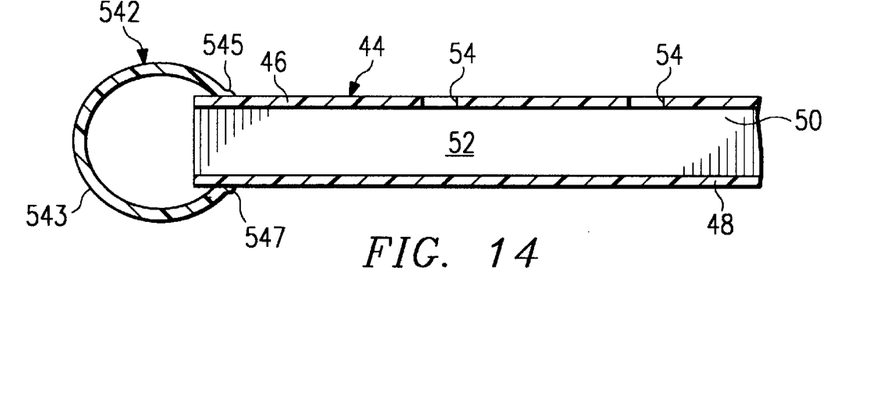
Figure 15:
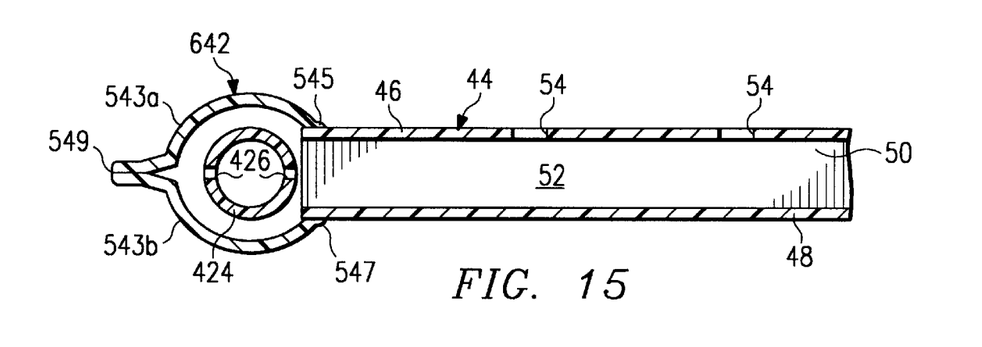

FIG. 14 shows fluid collection chamber 542 extending laterally along one edge of corrugated panel 44. Fluid collection chamber 542 is formed from a strip of material 543 having one edge 545 bonded to the exterior of first sheet 46 and an opposite edge 547 bonded to the exterior of second sheet 48. Fluid collection chamber 642 shown in FIG. 15 is formed in a manner similar to fluid collection chamber 542 of FIG. 14 except two strips of material 543a and 543b have been used. The strips of material 543a and 543b are joined with each other longitudinally at seam 549.

Figure 16:
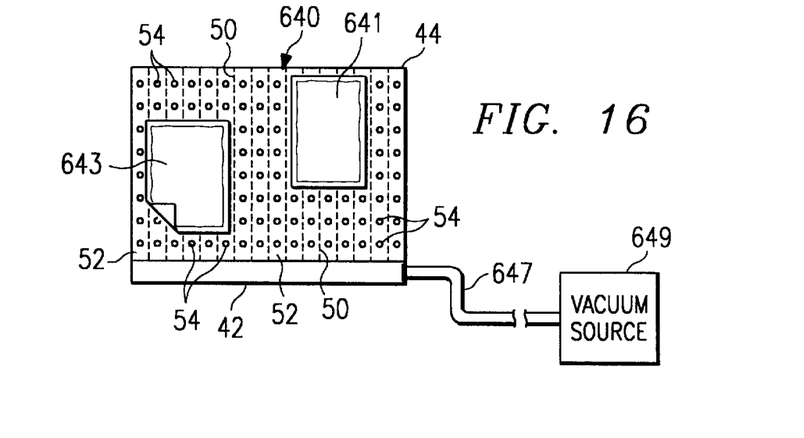
FIG. 16 is a schematic drawing showing a corrugated panel attached to a low level vacuum source for holding one or more sheets of photographic film during the film development process in accordance with further teachings of the present invention.

Vacuum pad 640 as shown in FIG. 16 may be used to releasably hold a sheet of paper 641, other flat materials, or a piece of photographic film 643. Vacuum pad 640 may be formed from a corrugated panel 44 as previously described with respect to vacuum pads 40 and 140. Conduit 647 is provided to couple manifold 42 with vacuum source 649. For some applications, vacuum source 649 may be a home vacuum cleaner. Vacuum pads 640 is particularly appropriate for use in photographic film developing laboratories.

Although the present invention and its advantages have been described in detail, it should be understood that various changes, substitutions and modifications can be made without departing from the spirit and scope of the invention as defined by the following claims.

What is claimed is:

1. A disposable vacuum pad for use during medical procedures to collect potentially hazardous fluids comprising:

a corrugated panel having edges and an interior volume defined by a first sheet and a second sheet with a plurality of ribs disposed within said interior volume and attached to the first sheet and the second sheet as an integral part thereof;

said ribs defining a plurality of fluid flow channels formed between the first sheet and the second sheet running generally continuously from one said edge to another said edge of said panel;

each said fluid flow channel comprising a plurality of openings formed in the first sheet generally along the length of said channel to allow fluid communication between the exterior of the first sheet and the respective fluid flow channels along the length thereof; and a manifold coupled with the fluid flow channels to communicate a source of vacuum with the fluid flow channels to draw a potentially hazardous fluid from the exterior of the vacuum pad through the holes in the first sheet, the fluid flow channels and into the manifold.

2. The disposable vacuum pad of claim 1 further comprising the corrugated panel formed from plastic material.

3. The disposable vacuum pad of claim 1 further comprising:

the corrugated panel having a generally rectangular configuration with a fluid seal, to prevent communication of potentially hazardous fluids formed around the perimeter of the corrugated panel between the first sheet and the second sheet; and the second sheet providing a generally fluid impervious barrier with respect to potentially hazardous fluid contained within the fluid flow channels.

4. The disposable vacuum pad of claim 1 further comprising:

a first manifold attached to one end of each fluid flow channel to communicate the source of vacuum between the first manifold and the respective fluid flow channels; and a second manifold attached to the ends of each fluid flow channel opposite from the first manifold to communicate the source of vacuum between the second manifold and the respective fluid flow channels.

5. The disposable vacuum pad of claim 4 further comprising:

a flexible conduit having a first portion and a second portion extending from one end of the flexible conduit;

the first portion of the flexible conduit connected with the first manifold to communicate potentially hazardous fluids therewith;

the second portion of the flexible conduit connected with the second manifold to communicate potentially hazardous fluids therewith; and the flexible conduit attached to a source of vacuum to draw potentially hazardous fluids from the exterior of the disposable vacuum pad through the holes in the first sheet into the fluid flow channels and the first manifold and the second manifold.

6. The disposable vacuum pad of claim 1 further comprising:

the corrugated panel having a generally rectangular configuration with four edges;

the manifold coupled with the fluid flow channels along only one edge of the corrugated panel; and a fluid seal formed along the edge of the corrugated panel opposite from the manifold to prevent communication of potentially hazardous fluids between the respective fluid flow channels and the exterior of the vacuum pad.

7. The disposable vacuum pad of claim 1 further comprising a conduit attached to the manifold for use in connecting the manifold with the source of vacuum.

8. The disposable vacuum pad of claim 1 wherein the conduit comprises flexible material.

9. A vacuum pad for collecting potentially hazardous fluids comprising:

a corrugated panel having a first sheet and a second sheet with a plurality of corrugated ribs disposed between the first sheet and the second sheet;

a plurality of fluid flow channels formed between the first sheet and the second sheet by the respective corrugated ribs;

each fluid flow channel having a first end and a second end with the respective fluid flow channel extending longitudinally therebetween;

a plurality of openings formed in the first sheet to allow fluid communication between the exterior of the first sheet and respective fluid flow channels;

a first manifold connected to the first end of each fluid flow channel to communicate a source of vacuum with the fluid flow channels to draw a fluid from the exterior of the vacuum pad through the holes in the first sheet, the fluid flow channels and into the first manifold;

a second manifold connected to the second end of each fluid flow channel opposite from the first manifold to communicate the source of vacuum with the fluid flow channels to draw a fluid from the exterior of the vacuum pad through the holes in the first sheet, the fluid flow channels and into the second manifold;

a fold formed in the corrugated panel extending laterally across the fluid flow channels; and the fold spaced longitudinally between the first manifold and the second manifold.

10. A vacuum pad for collecting fluids comprising:

a corrugated panel having a first sheet and a second sheet with a plurality of corrugated ribs disposed between the first sheet and the second sheet;

a plurality of fluid flow channels formed between the first sheet and the second sheet by the respective corrugated ribs;

a plurality of openings formed in the first sheet to allow fluid communication between the exterior of the first sheet and respective fluid flow channels;

a manifold attached to the fluid flow channels to communicate a source of vacuum with the fluid flow channels to draw a fluid from the exterior of the vacuum pad through the holes in the first sheet, the fluid flow channels and into the manifold;

the corrugated panel having a geometric configuration with at least four edges;

the manifold attached to the fluid flow channels along one edge of the corrugated panel;

a fluid seal formed along another edge of the corrugated panel opposite from the manifold to prevent undesired fluid communication between the respective fluid flow channels and the exterior of the vacuum pad; and the seal along the opposite edge of the corrugated panel further comprising a tapered portion extending at an angle from the first sheet to the second sheet.

11. A system having a disposable vacuum pad for use during medical procedures to collect potentially hazardous fluids comprising:

a corrugated plastic panel having edges and a first sheet and a second sheet with a plurality of ribs disposed between the first sheet and the second sheet;

a plurality of fluid flow channels formed between the first sheet and the second sheet by the respective ribs running generally continuously from one said edge to another said edge of said panel;

a plurality of openings formed in the first sheet generally along the length of each said channel to allow fluid communication between the exterior of the disposable vacuum pad and respective fluid flow channels along the length thereof;

a manifold coupled to the fluid flow channels to communicate potentially hazardous fluid between the manifold and the fluid flow channels; and a conduit coupled to the manifold whereby a source of vacuum may be connected to the manifold to draw potentially hazardous fluids from the exterior of the disposable vacuum pad through the holes in the first sheet, the respective fluid flow channels and the manifold into the conduit.

12. The system of claim 11 further comprising:

a fluid barrier formed around the perimeter of the corrugated plastic panel between the first sheet and the second sheet; and the second sheet providing a generally fluid impervious barrier with respect to potentially hazardous fluids contained within the fluid flow channels.

13. The system of claim 11 further comprising:

a first manifold attached to one end of each fluid flow channel to communicate potentially hazardous fluid between the respective fluid flow channels and the first manifold;

a second manifold attached to the end of each fluid flow channel opposite from the first manifold to communicate potentially hazardous fluid between the respective fluid flow channels and the second manifold;

a conduit having a first portion and a second portion extending therefrom;

the first portion of the conduit connected with the first manifold to communicate potentially hazardous fluids therewith;

the second portion of the conduit connected with the second manifold to communicate potentially hazardous fluids therewith; and the conduit attached to a source of vacuum to draw potentially hazardous fluids from the exterior of the disposable vacuum pad through the holes in the first sheet into the fluid flow channels and the first manifold and the second manifold.

14. The system of claim 11 further comprising:

the corrugated plastic panel having a generally rectangular configuration with four edges;

the manifold coupled to the fluid flow channels along only one of the edges of the corrugated plastic panel; and a fluid seal formed along another edge of the corrugated plastic panel opposite from the manifold to prevent communication of potentially hazardous fluids between the respective fluid flow channels and the exterior of the disposable vacuum pad through the opposite edge.

15. The system of claim 11 wherein the corrugated plastic panel further comprises a thickness in the range of one millimeter to twenty millimeters.

16. The system of claim 11 wherein the conduit further comprises:

one end of a first, flexible conduit attached to the manifold;

the other end of the first, flexible conduit attached to a disposable container; and a second conduit attached to the container and to the source of vacuum whereby any potentially hazardous liquids flowing through the first, flexible conduit will fall into and remain within the disposable container.

17. The system of claim 11 further comprising:

the conduit having a perforated portion which extends into the manifold; and a seal formed around the exterior of the flexible conduit adjacent to the perforated portion to prevent undesired potentially hazardous fluid flow from the manifold along the exterior of the flexible conduit.

18. The system of claim 11 further comprising:

a second corrugated plastic panel having a first sheet and a second sheet with a plurality of corrugated ribs disposed between the first sheet and the second sheet;

a plurality of fluid flow channels formed between the first sheet and the second sheet of the second corrugated plastic panel by the respective corrugated ribs;

a plurality of openings formed in the first sheet of the second corrugated plastic panel to allow potentially hazardous fluid communication between the exterior of the first sheet and the respective fluid flow channels of the second corrugated plastic panel; and the manifold attached to the fluid flow channels of the second corrugated plastic panel to communicate potentially hazardous fluid between the fluid flow channels of the second corrugated plastic panel and the manifold.

19. A system having a disposable vacuum pad for use during medical procedures to collect potentially hazardous fluids comprising:

a corrugated plastic panel having a first sheet and a second sheet with a plurality of corrugated ribs disposed between the first sheet and the second sheet;

a plurality of fluid flow channels formed between the first sheet and the second sheet by the respective corrugated ribs;

a plurality of openings formed in the first sheet to allow fluid communication between the exterior of the disposable vacuum pad and respective fluid flow channels;

a manifold coupled to the fluid flow channels to communicate potentially hazardous fluid between the manifold and the fluid flow channels;

a conduit coupled to the manifold whereby a source of vacuum may be connected to the manifold to draw potentially hazardous fluids from the exterior of the disposable vacuum pad through the holes in the first sheet, the respective fluid flow channels and the manifold into the conduit;

a layer of adhesive material disposed on the exterior surface of the second sheet of the corrugated plastic panel; and a removable protective cover disposed on the layer of adhesive material opposite from the second sheet of the corrugated plastic panel.

20. A system including a vacuum pad for use during a medical procedure to collect fluids comprising:

a corrugated plastic panel having a first sheet and a second sheet with a plurality of corrugated ribs disposed between the first sheet and the second sheet;

a plurality of fluid flow channels formed between the first sheet and the second sheet by the respective corrugated ribs;

a plurality of openings formed in the first sheet to allow fluid communication between the exterior of the vacuum pad and respective fluid flow channels;

a first manifold coupled with one end of each fluid flow channel to communicate fluid between the respective fluid flow channels and the first manifold;

a second manifold coupled with another end of each fluid flow channel opposite from the first manifold to communicate fluid between the respective fluid flow channels and the second manifold;

a conduit having a first portion and a second portion extending therefrom;

the first portion of the conduit connected with the first manifold to communicate fluids therewith;

the second portion of the conduit connected with the second manifold to communicate fluids therewith;

the conduit attached to a source of vacuum to draw a fluid from the exterior of the vacuum pad through the holes in the first sheet into the fluid flow channels, the first manifold, the second manifold and into the conduit;

a flexible seam formed in the corrugated plastic panel extending laterally across the fluid flow channels; and the flexible seam spaced longitudinally between and approximately parallel with the first manifold and the second manifold.

21. A system including a disposable vacuum pad for use during medical procedures to collect potentially hazardous fluids comprising:

a first corrugated plastic panel having edges and an interior volume defined by a first sheet and a second sheet with a plurality of ribs disposed within said interior volume between the first sheet and the second sheet as an integral part thereof;

said ribs defining a plurality of fluid flow channels formed between the first sheet and the second sheet by the respective corrugated ribs, said channels having a first end along one said edge and running to a second end along another said edge of said panel;

a plurality of openings formed in the first sheet, to allow potentially hazardous fluid communication between the exterior of the disposable vacuum pad and the respective fluid flow channels along the length thereof;

the second sheet providing a generally impervious barrier with respect to any potentially hazardous fluids within the fluid flow channels;

a first manifold attached to one said end of each fluid flow channel to communicate potentially hazardous fluid between the respective fluid flow channels and the manifold;

a seal formed along the another said end of each fluid flow channel opposite from the first manifold; and a flexible conduit attached to the first manifold whereby a source of vacuum may be connected with the first manifold to draw potentially hazardous fluid from the exterior of the disposable vacuum pad through the holes in the first sheet into the respective fluid flow channels through the first manifold and into the flexible conduit.

22. The system of claim 21 further comprising:

a second corrugated plastic panel having a first sheet and a second sheet with a plurality of corrugated ribs disposed between the first sheet and the second sheet as an integral part thereof;

the first manifold attached to one end of each fluid flow channel of the second corrugated plastic panel to communicate potentially hazardous fluid between the respective fluid flow channels and the first manifold; and a seal formed along another end of each fluid flow channel of the second corrugated plastic sheet opposite from the first manifold.

23. The system of claim 21 wherein the flexible conduit further comprises a hose formed from disposable material.

24. The system of claim 21 further comprising a layer of liquid absorbent material disposed on the exterior of the first sheet of the first corrugated plastic panel.

25. The system of claim 21 further comprising a layer of absorbent, heat sealable, non-woven material disposed on the exterior of the first sheet of the first corrugated plastic panel.

26. A system including a vacuum pad for collecting potentially hazardous fluids comprising:

a first corrugated plastic panel having a first sheet and a second sheet with a plurality of corrugated ribs disposed between the first sheet and the second sheet as an integral part thereof;

a plurality of fluid flow channels formed between the first sheet and the second sheet by the respective corrugated ribs;

a plurality of openings formed in the first sheet to allow fluid communication between the exterior of the vacuum pad and respective fluid flow channels;

the second sheet providing a generally impervious barrier with respect to any fluids within the fluid flow channels;

a first manifold attached to one end of each fluid flow channel to communicate fluid between the respective fluid flow channels and the first manifold;

a seal formed along another end of each fluid flow channel opposite from the first manifold;

a flexible hose attached to the first manifold whereby a source of vacuum may be connected with the first manifold to draw fluid from the exterior of the vacuum pad through the holes in the first sheet into the respective fluid flow channels through the first manifold and into the flexible hose;

a layer of liquid absorbent material disposed on the exterior surface of the first sheet of the first corrugated plastic panel;

a barrier layer disposed between the layer of liquid absorbent material and the first sheet of the first corrugated plastic panel; and the barrier layer formed from material which allows liquids to flow in one direction from the exterior of the vacuum pad through the barrier layer and substantially blocks the flow of liquids from the vacuum pad outwardly through the barrier layer.

27. A system including a vacuum pad for collecting potentially hazardous fluids comprising:

a first corrugated plastic panel having a first sheet and a second sheet with a plurality of corrugated ribs disposed between the first sheet and the second sheet as an integral part thereof;

a plurality of fluid flow channels formed between the first sheet and the second sheet by the respective corrugated ribs;

a plurality of openings formed in the first sheet to allow fluid communication between the exterior of the vacuum pad and respective fluid flow channels;

the second sheet providing a generally impervious barrier with respect to any fluids within the fluid flow channels;

a first manifold attached to one end of each fluid flow channel to communicate fluid between the respective fluid flow channels and the manifold;

a seal formed along another end of each fluid flow channel opposite from the first manifold;

a flexible conduit attached to the first manifold whereby a source of vacuum may be connected with the first manifold to draw fluid from the exterior of the vacuum pad through the holes in the first sheet into the respective fluid flow channels through the first manifold and into the flexible conduit;

a layer of wicking material disposed on the exterior of the first sheet of the first corrugated plastic panel; and a barrier layer disposed on the wicking layer opposite from the first sheet of the first corrugated plastic panel whereby the layer of wicking material will draw liquids through the barrier layer and the barrier layer will prevent liquids from flowing outwardly from the layer of wicking material.

28. A vacuum pad for collecting potentially hazardous fluids comprising:

a corrugated panel having a first sheet and a second sheet with a plurality of corrugated ribs disposed between the first sheet and the second sheet;

a plurality of fluid flow channels formed between the first sheet and the second sheet by the respective corrugated ribs;

a plurality of openings formed in the first sheet to allow fluid communication between the exterior of the first sheet and respective fluid flow channels;

a manifold attached to the fluid flow channels to communicate a source of vacuum with the fluid flow channels to draw a fluid from the exterior of the vacuum pad through the holes in the first sheet, the fluid flow channels and into the manifold;

a layer of wicking material disposed on the exterior of the first sheet of the corrugated panel; and a barrier layer disposed on the wicking layer opposite from the first sheet of the corrugated panel whereby the layer of wicking material will draw any liquids in the fluid through the barrier layer and the barrier layer will restrict the liquids from flowing outwardly from the layer of wicking material.

* * * * *